United States Patent
Shetty

(10) Patent No.: US 11,045,512 B2
(45) Date of Patent: Jun. 29, 2021

(54) HERBAL COMPOSITION FOR THE TREATMENT AND MANAGEMENT OF THYROID DYSFUNCTION AND METHOD OF PREPARATION THEREOF

(71) Applicant: Muniyal Ayurvedic Research Centre, Manipal (IN)

(72) Inventor: M Vijayabhanu Shetty, Manipal (IN)

(73) Assignee: Muniyal Ayurvedic Research Centre, Manipal (IN)

(*) Notice: Subject to any disclaimer, the term of this patent is extended or adjusted under 35 U.S.C. 154(b) by 89 days.

(21) Appl. No.: 16/229,471

(22) Filed: Dec. 21, 2018

(65) Prior Publication Data

US 2019/0111094 A1 Apr. 18, 2019

Related U.S. Application Data

(60) Provisional application No. 62/609,953, filed on Dec. 22, 2017.

(51) Int. Cl.
| | | |
|---|---|---|
| *A61K 36/48* | (2006.01) | |
| *A61K 35/04* | (2006.01) | |
| *A61K 35/614* | (2015.01) | |
| *A61K 33/34* | (2006.01) | |
| *A61K 33/00* | (2006.01) | |
| *A61P 5/14* | (2006.01) | |
| *A61K 33/30* | (2006.01) | |
| *A61K 36/328* | (2006.01) | |
| *A61K 36/185* | (2006.01) | |
| *A61K 9/20* | (2006.01) | |
| *A61K 33/26* | (2006.01) | |

(52) U.S. Cl.
CPC ............... *A61K 36/48* (2013.01); *A61K 9/20* (2013.01); *A61K 9/205* (2013.01); *A61K 33/00* (2013.01); *A61K 33/26* (2013.01); *A61K 33/30* (2013.01); *A61K 33/34* (2013.01); *A61K 35/04* (2013.01); *A61K 35/614* (2013.01); *A61K 36/185* (2013.01); *A61K 36/328* (2013.01); *A61P 5/14* (2018.01)

(58) Field of Classification Search
None
See application file for complete search history.

(56) References Cited

PUBLICATIONS

By Samy et al. "A compilation of bioactive compounds from Ayurveda", Bioinformation 3(3): 100-110 (Year: 2008).*
Chandran et al. "Shilajatu and Swarna Makshika—A promising ayurvedic combination in management of diabetes", Journal of Ayurvedic and Herbal Medicine, 2(3): 96-99 (Year: 2016).*

(Continued)

*Primary Examiner* — Isis A Ghali
(74) *Attorney, Agent, or Firm* — Pilloff Passino & Cosenza LLP; Sean A. Passino; Rachel K. Pilloff

(57) ABSTRACT

Herbal composition for treatment and management of Thyroid dysfunction and method of preparation are disclosed herein. The disclosed composition including herbs and bhasmas may be used to treat Thyroid dysfunction and associated complications such as Hashimoto's thyroiditis, hyperthyroidism, hypothyroidism, Goiter, Thyrotoxicosis, Graves' disease, autoimmune thyroiditis etc. The method disclosed herein may be used as the main line of treatment or as supportive medication.

12 Claims, 6 Drawing Sheets

(56) References Cited

PUBLICATIONS

Kar "Fruit extract of Emblica officinalis ameliorates hyperthyroidism and hepatic lipid peroxidation in mice", Pharmazie 58: 753-755 (Year: 2003).*
Shirwaikar et al. "Herbal excipient in novel drug delivery system", Indian Journal of Pharmaceutical Sciences (Year: 2008).*
The Government of India, Biological Diversity Act, 2002.

* cited by examiner

HERBAL COMPOSITION FOR THE TREATMENT AND MANAGEMENT OF THYROID DYSFUNCTION AND METHOD OF PREPARATION THEREOF

CROSS REFERENCE TO RELATED APPLICATION

This application is based on and derives the benefit of U.S. Provisional Application 62/609,953 filed on Dec. 22, 2017 the contents of which are incorporated herein by reference in their entirety.

TECHNICAL FIELD

The embodiments disclosed in this specification relates to herbal composition effective in treatment and management of Thyroid dysfunction and associated complications. It also relates to the process for preparation of such composition.

BACKGROUND

Thyroid glands, the endocrine glands sitting in the neck wrapping around the wind pipe, play a critical role in metabolic and cardiovascular activities of the body. Thyroid glands are capable of regulating these vital activities through hormones viz. Triiodothyronine (T3) and Thyroxine (T4).

The hypothalamus and pituitary glands are crucial in the functioning of the thyroid glands. They communicate with each other and the thyroid glands in order to maintain T3 and T4 levels. The TRH (TSH releasing hormone) produced by hypothalamus signals the release of TSH (Thyroid-stimulating hormone) by pituitary glands, which further regulates the levels of thyroid hormones.

The levels of T3 and T4 are indicative of an ill functioning thyroid gland. Further, a defective pituitary gland may also lead to thyroid hormone imbalance. Regardless of the reason, the over or under production of these Thyroid hormones lead to thyroid disorders.

Hyperthyroidism is a case of increased levels of thyroid hormones, the causes of which include Graves' disease, tumors of the thyroid glands and toxic adenomas of thyroid glands. Reduced levels of thyroid hormones is a case of Hypothyroidism which may be caused by Hashimoto's disease, Iodine deficiency, etc. Such thyroid hormone imbalance can lead to hypertension, heart failure, etc.

Various methods of managing T3 and T4 imbalance are known. These methods include hormone supplementation, anti-thyroid drugs, surgery, etc. However, such allopathic interventions have been known to have side effects.

Alternatively, ayurvedic treatment methods have also been developed to treat thyroid disorders. The knowledge of using Ashwagandha, Kanchanara guggulu, *Coleus forskohlii*, primrose oil, *Pistia stratiotes* etc in restoring the normal functioning of Thyroid glands is ancient and has been used to formulate various herbal compositions. However, the effectiveness of such herbal therapies may not always meet expectations. There exists a need for an effective method of treating and managing Thyroid disorders.

OBJECT OF THE DISCLOSED EMBODIMENTS

The principal object of the embodiments disclosed herein is to provide a method of treating Thyroid dysfunction and associated complications.

A second object of the embodiments disclosed herein is to provide a method of management of Thyroid dysfunction and associated complications.

Another object of the embodiments disclosed herein is to provide herbal composition and a method for its preparation.

These and other objects of the embodiments herein will be better appreciated and understood when considered in conjunction with the following description and the accompanying drawings. It should be understood, however, that the following descriptions, while indicating preferred embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF FIGURES

The embodiments disclosed herein are illustrated in the accompanying drawings. The embodiments herein will be better understood from the following description with reference to the drawings, in which.

DETAILED DESCRIPTION

Figure 1A:
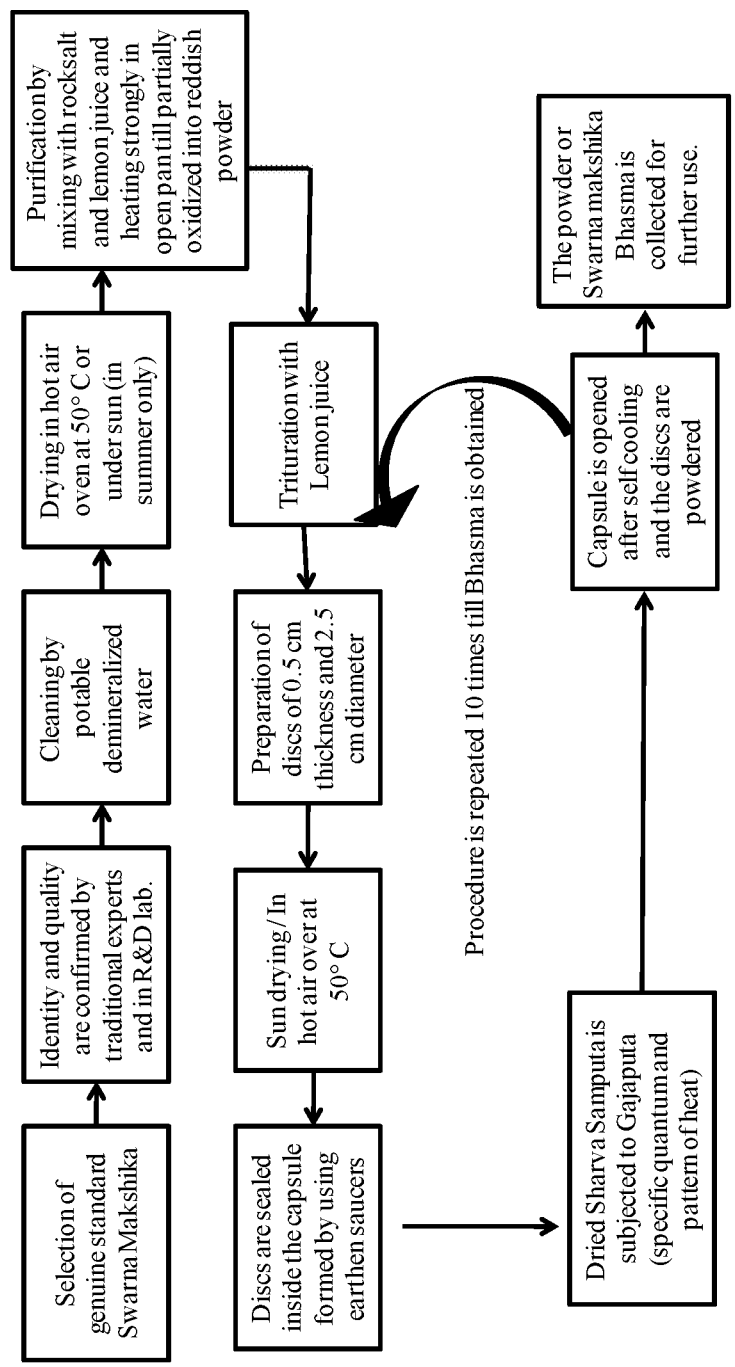
FIG. 1(a) depicts a flowchart for the preparation of Swarna Makshika Bhasma, according to the various embodiments herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those skilled in the art to practice the embodiments herein. Accordingly, the examples should not be construed as limiting the scope of the embodiments herein.

The embodiments herein achieve a herbal composition of therapeutic value, and a process for the preparation of the composition. The herbal composition disclosed herein is useful in the treatment and management of Thyroid dysfunction and associated complications. The composition, disclosed in the various embodiments herein, may be used to treat hypothyroidism, hyperthyroidism and any complications associated with thyroid. It has been observed that the Disclosed composition may also be instrumental in the management of autoimmune thyroiditis. Accordingly, the embodiments disclosed herein achieve a method for the treatment of Thyroid dysfunction and associated complications. The Disclosed composition, in various embodiments, may be used as a main line of treatment or as supportive medication in addition to other line of medication such as allopathy.

Composition

The disclosed embodiments herein provide a herbal composition having a combination of selected herbs and minerals. In an embodiment, the herbal composition includes herbs and minerals. In another embodiment, the herbal composition includes a herbs, minerals and a suitable excipient.

Herb

In an embodiment, the composition includes the herbs *Bauhinia variegata*, *Crataeva nurvala* and *Commiphora mukul* (also referred to as Guggulu), or their extracts, or the active ingredients extracted from these herbs. In another embodiment, the composition further includes at least one of the herbs selected from *Emblica officinalis*, *Terminalia chebula*, *Terminalia bellerica*, *Zingiber officinale*, *Piper nigrum*, *Piper longum*, *Cinnamomum zeylanica*, *Elettaria cardamomum*, *Cinnamomum tamala*, *Glycerrhiza glabra*, *Boerhavia diffusa*, *Adhtatoda vasica*, *Vinca rosea*, *Withania somnifera*, *Sida cordifolia*, *Tinospora cordifolia*, *Ocimum sanctum*, *Curcuma longa*, *Moringa oleifera*, *Aristolochia indica*, *Azadirachta indica* and *Eclipta alba*; or their extracts; or the active ingredients extracted from these herbs.

In an embodiment, the composition may include specific parts of the herb (also referred as herb component) such as roots, fruits, bark, stem, leaves, rhizome, etc. In an embodiment, the composition includes stem bark of *Bauhinia variegata*, *Crataeva nurvala*, *Cinnamomum zeylanica*, *Moringa oleifera* and *Azadirachta indica*; oleo gum resin of *Commiphora mukul*, fruits of *Emblica officinalis*, *Terminalia chebula*, *Terminalia bellerica*, *Piper nigrum* and *Piper longum*, rhizome of *Zingiber officinale*, *Glycerrhiza glabra* and *Curcuma longa*; seeds of *Elettaria cardamomum*; leaves of *Cinnamomum tamala*, *Vinca rosea* and *Ocimum sanctums*; roots of *Boerhavia diffusa*, *Adhtatoda vasica*, *Aristolochia indica*, *Withania somnifera* and *Sida cordifolia*; stem of *Tinospora cordifolia*; and whole plant of *Eclipta alba*; or their extract. However, it is also within the scope of the claims provided herein for the herbal composition to include other herb components such as leaf, flowers, etc. without otherwise deterring intended function of the poly herbal composition.

In an embodiment, the composition includes *Bauhinia variegata* in an amount ranging from 10 to 14 wt %, *Crataeva nurvala* in an amount ranging from 10 to 14 wt %, and *Commiphora mukul* in an amount ranging from 8 to 12 wt %, of the total weight of the composition. In another embodiment, the composition may further include *Emblica officinalis* in an amount ranging from 2 to 6 wt %, *Terminalia chebula* in an amount of ≤3 wt %, *Terminalia bellerica* in an amount of ≤3 wt %, *Zingiber officinale* in an amount of ≤3 wt %, *Piper nigrum* in an amount of ≤3 wt %, *Piper longum* in an amount of ≤3 wt %, *Cinnamomum zeylanica* in an amount of ≤3 wt %, *Elettaria cardamomum* in an amount of ≤3 wt %, *Cinnamomum tamala* in an amount of ≤3 wt %, *Glycerrhiza glabra* in an amount of ≤3 wt %, *Boerhavia diffusa* in an amount of ≤3 wt %, *Adhtatoda vasica* in an amount of ≤3 wt %, *Vinca rosea* in an amount of ≤3 wt %, *Withania somnifera* in an amount of ≤3 wt %, *Sida cordifolia* in an amount of ≤3 wt %, *Tinospora cordifolia* in an amount of ≤3 wt %, *Ocimum sanctum* in an amount of ≤3 wt %, *Curcuma longa* in an amount of ≤3 wt %, *Moringa oleifera* in an amount of ≤3 wt %, *Aristolochia indica* in an amount of ≤3 wt %, *Azadirachta indica* in an amount of ≤3 wt % and *Eclipta alba* in an amount of ≤2 wt %, of the total weight of the composition.

The herb component of the herbs, disclosed herein, maybe included in the composition in any form that is generally known in the field. For example, the herb component may be processed to form extracts, dried, powdered, pelleted, concentrated, etc. In an embodiment, the herb components are dried and powdered which is further incorporated into the composition. In another embodiment, the herb component may be an aqueous starch extract.

Minerals

In an embodiment, the composition includes minerals in the form of Bhasmas or calcined preparations such as Swarna Makshika bhasma, Abhraka bhasma, Loha bhasma, Trivanga bhasma, and Pravala bhasma. Alternatively, the composition may also include at least one mineral selected from a group consisting of mica, lead, tin, zinc, coral, iron and copper pyrite. In the disclosed embodiments, the bhasmas along with the herbs form bioavailable herbal complexes which are useful in treating Thyroid dysfunction and associated complications. In another embodiment, the composition includes *Shilajit*. However, it is also within the scope of claims provided herewith for the herbal composition to include, as a substitute or additionally, other similar calcined preparations or minerals without otherwise deterring the intended function of the herbal composition.

In an embodiment, the composition includes Swarna Makshika bhasma in an amount of ≤2 wt %, Abhraka bhasma in an amount of ≤2 wt %, Loha bhasma in an amount of ≤2 wt %, Trivanga bhasma in an amount of ≤2 wt % and Pravala bhasma in an amount of ≤2 wt %. In another embodiment, the mineral component includes *shilajit* in an amount in the range of 2 to 6 wt %.

The Disclosed composition, in the various embodiments herein, may further include a suitable excipient. The list of suitable excipients may include solvents, binders, lubricants, herbal carriers, oils and salts that are generally known in the art. In an embodiment, the excipient includes acacia gum.

Further, the amount of herb and mineral that may be included in the various embodiments of the disclosed composition may each be in the range of 0 to 14 wt %. In an embodiment, the composition includes *Bauhinia variegata* (10 to 14 wt %), *Crataeva nurvala* (10 to 14 wt %), *Commiphora mukul* (8 to 12 wt %) and *shilajit* (2 to 6 wt %), of the total weight of the composition.

In another embodiment, the composition includes *Bauhinia variegata* (10 to 14 wt %), *Crataeva nurvala* (10 to 14 wt %) and *Commiphora mukul* (8 to 12 wt %); at least one of *Emblica officinalis* (2 to 6 wt %), *Terminalia chebula* (≤3 wt %), *Terminalia bellerica* (≤3 wt %), *Zingiber officinale* (≤3 wt %), *Piper nigrum* (≤3 wt %), *Piper longum* (≤3 wt %), *Cinnamomum zeylanica* (≤3 wt %), *Elettaria cardamomum* (≤3 wt %), *Cinnamomum tamala* (≤3 wt %), *Glycerrhiza glabra* (≤3 wt %), *Boerhavia diffusa* (≤3 wt %), *Adhtatoda vasica* (≤3 wt %), *Vinca rosea* (≤3 wt %), *Withania somnifera* (≤3 wt %), *Sida cordifolia* (≤3 wt %), *Tinospora cordifolia* (≤3 wt %), *Ocimum sanctum* (≤3 wt %), *Curcuma longa* in an amount of ≤3 wt %, *Moringa oleifera* (≤3 wt %), *Aristolochia indica* (≤3 wt %), *Azadirachta indica* (≤3 wt %) and *Eclipta alba* (≤2 wt %); and at least one of Swarna Makshika bhasma (≤2 wt %), Abhraka bhasma (≤2 wt %), Loha bhasma (≤2 wt %), Trivanga bhasma (≤2 wt %) and Pravala bhasma (≤2 wt %), of the total weight of the composition.

In another embodiment, the composition includes *Bauhinia variegata* (10 to 14 wt %), *Crataeva nurvala* (10 to 14 wt %) and *Commiphora mukul* (8 to 12 wt %); at least one of *Emblica officinalis* (2 to 6 wt %), *Terminalia chebula* (≤3 wt %), *Terminalia bellerica* (≤3 wt %), *Zingiber officinale* (≤3 wt %), *Piper nigrum* (≤3 wt %), *Piper longum* (≤3 wt %), *Cinnamomum zeylanica* (≤3 wt %), *Elettaria cardamomum* (≤3 wt %), *Cinnamomum tamala* (≤3 wt %), *Glycerrhiza glabra* (≤3 wt %), *Boerhavia diffusa* (≤3 wt %), *Adhtatoda vasica* (≤3 wt %), *Vinca rosea* (≤3 wt %), *Withania somnifera* (≤3 wt %), *Sida cordifolia* (≤3 wt %), *Tinospora cordifolia* (≤3 wt %), *Ocimum sanctum* (≤3 wt %), *Curcuma longa* in an amount of ≤3 wt %, *Moringa oleifera* (≤3 wt %), *Aristolochia indica* (≤3 wt %), *Azadirachta indica* (≤3 wt %) and *Eclipta alba* (≤2 wt %); and at least one of Swarna Makshika bhasma (≤2 wt %), Abhraka bhasma (≤2 wt %), Loha bhasma (≤2 wt %), Trivanga bhasma (≤2 wt %), Pravala bhasma (≤2 wt %) and *shilajit* (2 to 6 wt %), of the total weight of the composition.

In another embodiment, the composition includes *Bauhinia variegata* (10 to 14 wt %), *Crataeva nurvala* (10 to 14 wt %), *Commiphora mukul* (8 to 12 wt %); at least one of *Emblica officinalis* (2 to 6 wt %), *Terminalia chebula* (≤3 wt %), *Terminalia bellerica* (≤3 wt %), *Zingiber officinale* (≤3 wt %), *Piper nigrum* (≤3 wt %), *Piper longum* (≤3 wt %), *Cinnamomum zeylanica* (≤3 wt %), *Elettaria cardamomum* (≤3 wt %), *Cinnamomum tamala* (≤3 wt %), *Glycerrhiza glabra* (≤3 wt %), *Boerhavia diffusa* (≤3 wt %), *Adhtatoda vasica* (≤3 wt %), *Vinca rosea* (≤3 wt %), *Withania somnifera* (≤3 wt %), *Sida cordifolia* (≤3 wt %), *Tinospora cordifolia* (≤3 wt %), *Ocimum sanctum* (≤3 wt %), *Curcuma longa* in an amount of ≤3 wt %, *Moringa oleifera* (≤3 wt %), *Aristolochia indica* (≤3 wt %), *Azadirachta indica* (≤3 wt %) and *Eclipta alba* (≤2 wt %); and at least one of Swarna Makshika bhasma (≤2 wt %), Abhraka bhasma (≤2 wt %), Loha bhasma (≤2 wt %), Trivanga bhasma (≤2 wt %), Pravala bhasma (≤2 wt %) and *shilajit* (2 to 6 wt %), of the total weight of the composition; and a suitable excipient. In an embodiment, the suitable excipient is acacia gum.

Further, the amount of gum acacia may be any amount suitable to perform the activity of an excipient. In an embodiment, the composition may include gum acacia in an amount in the range of 8 to 12 wt. %.

However, it is apparent that slight variations in the amount of the ingredients may be performed without otherwise deterring from the intended function of the herbo-mineral composition.

The herbal composition disclosed herein may be formulated in various dosage forms such that it is suitable for oral administration. The herbal composition may be in the form of tablets, pellets, lozenges, granules, capsules, solutions, emulsions, suspensions, or any other form suitable for use. In an embodiment, the herbal composition is formulated in the form of tablets, preferably 500 mg tablets. For example: Table IA depicts the quantities of each ingredient in a 500 mg tablet. All weight percentages provided herein are based on the total weight of the composition.

Further disclosed herein, is a tablet for treating cancer. In an embodiment, the tablet is a 500 mg tablet having herb component, mineral component and excipient as depicted in Table 1.

TABLE 1

Each 500 mg tablet includes:

| No. | Sanskrit Name | Part used | Latin/English name | Quantity(mg) | wt % |
|---|---|---|---|---|---|
| 1 | Kanchanara | Dry stem bark | *Bauhinia variegata* | 60 mg | 12 |
| 2 | Varuna | Dry stem bark | *Crataeva nurvala* | 60 mg | 12 |
| 3 | Shuddha Guggulu | Oleo-gum-resin | *Commiphora mukul* | 50 mg | 10 |
| 4 | Amalaki | dry fruits | *Emblica officinalis* | 20 mg | 4 |
| 5 | Hareetaki | dry fruits | *Terminalia chebula* | 10 mg | 2 |
| 6 | Vibhitaki | dry fruits | *Terminalia bellerica* | 10 mg | 2 |
| 7 | Shunthi | Dry rhizome | *Zingiber officinale* | 10 mg | 2 |
| 8 | Maricha | Dry fruits | *Piper nigrum* | 10 mg | 2 |
| 9 | Pippali | dry fruits | *Piper longum* | 10 mg | 2 |
| 10 | Tvak | Dry stem bark | *Cinnamomum zeylanica* | 10 mg | 2 |
| 11 | Ela | Dry seeds | *Elettaria cardamomum* | 10 mg | 2 |
| 12 | Patra | Dry leaves | *Cinnamomum tamala* | 10 mg | 2 |
| 13 | Shilajatu | Fossil resin | *Asphaltum punjabicanum* | 20 mg | 4 |
| 14 | Yashtimadhu | Dry rhizome | *Glycerrhiza glabra* | 10 mg | 2 |
| 15 | Punarnava | Dry root | *Boerhavia diffusa* | 10 mg | 2 |
| 16 | Vasa | Dry root | *Adhtatoda vasica* | 10 mg | 2 |
| 17 | Sadapushpa | Dry leaves | *Vinca rosea* | 10 mg | 2 |
| 18 | Ashvagandha | Dry root | *Withania somnifera* | 10 mg | 2 |
| 19 | Bala | Dry root | *Sida cordifolia* | 10 mg | 2 |
| 20 | Guduchi Satva | Aqueous starch extract of stem | *Tinospora cordifolia* | 10 mg | 2 |
| 21 | Tulasi | Dried leaves | *Ocimum sanctum* | 10 mg | 2 |
| 22 | Haridra | Dry rhizome | *Curcuma longa* | 10 mg | 2 |
| 23 | Guduchi | Dry stem | *Tinospora cordifolia* | 10 mg | 2 |
| 24 | Shigru | Dry stem bark | *Moringa oleifera* | 10 mg | 2 |
| 25 | Ishwari | Dried root | *Aristolochia indica* | 10 mg | 2 |
| 26 | Nimba | Dry stem bark | *Azadirachta indica* | 10 mg | 2 |
| 27 | Bhringaraja | Dried whole plant | *Eclipta alba* | 5 mg | 1 |
| 28 | Trivanga bhasma | Incinerated metals | Incinerated tin, lead and zinc | 5 mg | 1 |
| 29 | Abhraka bhasma | Incinerated mineral | Incinerated mica | 5 mg | 1 |
| 30 | Swarnamakshika bhasma | Incinerated ore | Incinerated copper pyrite | 5 mg | 1 |
| 31 | Pravala hasma | Incinerated coral | Incinerated coral | 5 mg | 1 |

TABLE 1-continued

Each 500 mg tablet includes:

| No. | Sanskrit Name | Part used | Latin/English name | Quantity(mg) | wt % |
| --- | --- | --- | --- | --- | --- |
| 32 | Loha Bhasma | Incinerated metal | Calx of iron | 5 mg | 1 |
| 33 | Excipient | Resin | Gum acacia | 50 mg | 10 |

In an embodiment, the disclosed composition is a blackish brown biconvex shaped tablet having the characteristics as depicted in Table 2. The invention is further described by reference to the following table by way of illustration only, and should not be construed to limit the scope of the present invention. It will be apparent to those skilled in the art that many modifications may be practiced without departing from the scope of the present invention.

TABLE 2

| Test Parameters | Specifications |
| --- | --- |
| Description | Blackish brown biconvex shaped tablets |
| Identification | Tests positive for piperine, guggulusteron. |
| Average weight | 500 mg ± 12.5 mg |
| Uniformity of weight | ±2.5% of actual average weight |
| Average tablet hardness | 2.0 kg/cm$^2$ |
| Loss on drying | 3.7% w/w |
| Methanol soluble extractive | 28.9% w/v |
| Chloroform soluble extractive | 7.9% w/v |
| Let Ash value | 18.0% w/w |
| Average Tablet Disintegration time | 28 minutes |

Method

Disclosed herein are embodiments of a method of preparing the herbal composition. In an embodiment, the method includes, levigating processed bhasma, guggulu and *shilajit* in a grinder, adding finely powdered herbs into the grinder, and adding grinding decoction while continuing grinding to obtain the composition.

In an embodiment, the process further includes mixing the obtained composition with an excipient such as gum acacia and grinding for a period of 1 to 3 hours; and drying of the obtained mass at a temperature in the range of 40 to 60 degree Celsius. Further, the obtained mass may be subjected to wet granulation followed by punching into 500 mg tablets.

The bhasmas include at least one of Abhraka Bhasma, Pravala Bhasma, Loha Bhasma, Trivanga Bhasma and Swarna Makshika Bhasma. The mixture of bhasmas, guggulu and *shilajit* may be in semi solid form. In an embodiment, the levigation may be performed for a duration of around 3 hours.

Further, the finely powdered herbs include finely powdered dry stem bark of *Bauhinia variegata, Crataeva nurvala, Cinnamomum zeylanica, Moringa oleifera* and *Azadirachta indica*; fruits of *Emblica officinalis, Terminalia chebula, Terminalia bellerica, Piper nigrum* and *Piper longum*, rhizome of *Zingiber officinale, Glycerrhiza glabra* and *Curcuma longa*; seeds of *Elettaria cardamomum*; leaves of *Cinnamomum tamala, Vinca rosea* and *Ocimum sanctum*, roots of *Boerhavia diffusa, Adhtatoda vasica, Aristolochia indica, Withania somnifera* and *Sida cordifolia*; aqueous starch extract of stem and dry stem of *Tinospora cordifolia* and whole plant of *Eclipta alba*.). In an embodiment, finely powdered herbs may be obtained by powdering and sieving the herb components at 80 mesh.

The grinding decoction is a decoction of herbs (also referred as grinding herbs) that may facilitate grinding. In an embodiment, the grinding decoction includes a decoction of at least one herb selected from a list consisting of: *Embilca officinalis, Terminalia chebula, Terminalia bellerica, Crataeva nurvala, Bauhinia variegate, Steriospermum suaveolens, Premna mucronate, Gmelina arborea, Aegle marmelos, Oroxylum indicum, Desmodium gangeticum, Uraria picta, Solanum indicum, Solanum xanthocarpum, Tribulus terrestris, Vinca rosea, Cynadon dactylon, Rubia cordifolia, Acacia catechu, Adhatoda vasica, Eclipta alba, Moringa oleifera, Cuminum cyminum, Mimosa pudica, Calotropis procera, Sida cordifolia, Trichosanthes dioica, Tinospora cordifolia, Asparagus racemosus, Ocimum sanctum* and *Murraya koeinigii*

The decoction may be obtained by any method of decocting generally known in the field. In an embodiment, the method of preparation of grinding decoction includes:

soaking the grinding herbs. For example, soaking powdered dry fruit of *Embilca officinalis, Tribulus terrestris, Terminalia chebula* and *Terminalia bellerica*; dry stem bark of *Crataeva nurvala, Moringa oleifera* and *Bauhinia variegate*; dry roots of *Steriospermum suaveolens, Calotropis procera, Sida cordifolia, Rubia cordifolia, Premna mucronate, Gmelina arborea, Aegle marmelos, Solanum indicum* and *Oroxylum indicum*; dry plant of *Desmodium gangeticum, Uraria picta* and *Solanum xanthocarpum*, fresh leaves of *Vinca rosea, Ocimum sanctum, Murraya koeinigii* and *Adhatoda vasica*; fresh whole plant of *Cynadon dactylon, Trichosanthes dioica* and *Eclipta alba*; dry heartwood of *Acacia catechu*; dry cremocarp of *Cuminum cyminum*; dry whole plant of *Mimosa pudica*; fresh stem of *Tinospora cordifolia*; and fresh root of *Asparagus racemosus*; and concentrating the soaked herb mixture.

In an embodiment, soaking may be performed by soaking the grinding herbs in 16 parts of water overnight. In a further embodiment, concentrating may be performed by boiling at high temperature, preferably about 80° C. to 85° C., until ⅛th of the liquid remains. Concentration may be confirmed with the help of Brix meter.

Figure 2:
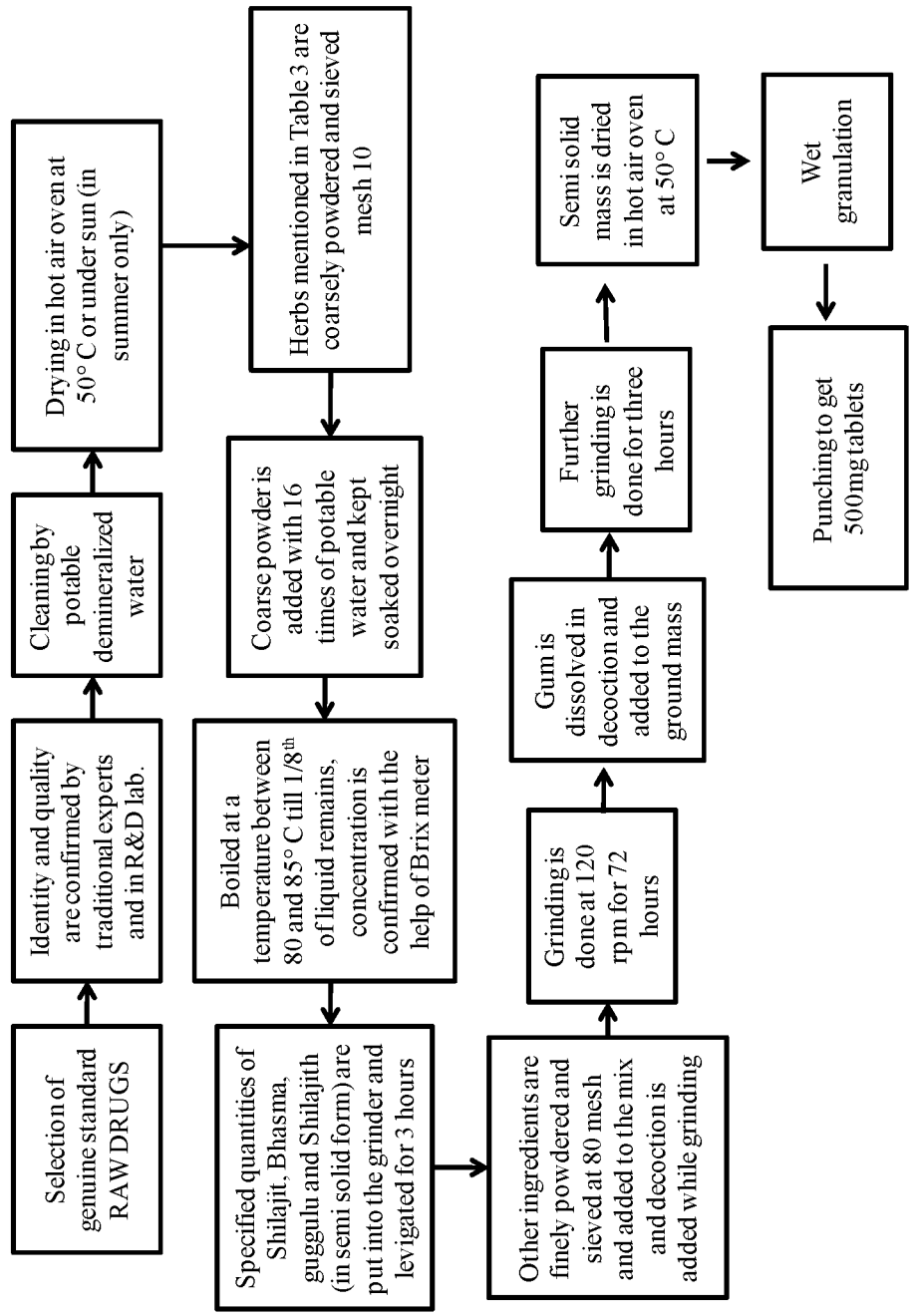
FIG. 2 depicts a flowchart for the preparation of fortified tablets, according to embodiments as disclosed herein.

Further, once the grinding decoction is added grinding is continued. In an embodiment, grinding is continued for about 72 hours, preferably at about 120 rpm, to obtain a ground mass. In an embodiment, gum acacia may be added to the obtained composition by dissolving in the grinding decoction while continuing grinding for 3 hours to obtain a semisolid mass. In another embodiment, the method further includes drying the obtained mass at about 60 degree Celsius, preferably in a hot air oven, to obtain a composition disclosed in the various embodiments herein. In another embodiment, the method may further include wet granulating and punching of the obtained mass to obtain 500 mg tablets. FIG. 2 depicts a flowchart for the preparation of fortified tablets. Table 2 depicts the Herb ingredients required for grinding (grinding herbs) in one of the preferred embodiments.

TABLE 3

Decoction of following herbs:

| | | | |
|---|---|---|---|
| 1 | Amalaki dry fruits | Embilca officinalis | 1 part |
| 2 | Hareetaki dry fruits | Terminalia chebula | 1 part |
| 3 | Vibhitaki dry fruits | Terminalia bellerica | 1 part |
| 4 | Varuna Dry stem bark | Crataeva nurvala | 1 part |
| 5 | Kanchanara Dry stem bark | Bauhinia variegata | 1 part |
| 6 | Patala dry root | Steriospermum suaveolens | 1 part |
| 7 | Agnimantha dry root | Premna mucronata | 1 part |
| 8 | Gambhari dry root | Gmelina arborea | 1 part |
| 9 | Bilva dry root | Aegle marmelos | 1 part |
| 10 | Shyonaka dry root | Oroxylum indicum | 1 part |
| 11 | Shalaparni dry plant | Desmodium gangeticum | 1 part |
| 12 | Prshniparni dry plant | Uraria picta | 1 part |
| 13 | Brhati dry root | Solanum indicum | 1 part |
| 14 | Kantakari dry plant | Solanum xanthocarpum | 1 part |
| 15 | Gokshura dry fruit | Tribulus terrestris | 1 part |
| 16 | Sadapushpa fresh leaves | Vinca rosea | 1 part |
| 17 | Durva fresh whole plant | Cynadon dactylon | 1 part |
| 18 | Manjishtha dried root | Rubia cordifolia | 1 part |
| 19 | Khadira dried heartwood | Acacia catechu | 1 part |
| 20 | Vasa fresh leaves | Adhatoda vasica | 1 part |
| 21 | Bhringaraja fresh whole plant | Eclipta alba | 1 part |
| 22 | Shigru dried stem bark | Moringa oleifera | 1 part |
| 23 | Jeeraka dried cremocarp | Cuminum cyminum | 1 part |
| 24 | Lajjalu dried whole plant | Mimosa pudica | 1 part |
| 25 | Arka dry root | Calotropis procera | 1 part |
| 26 | Bala dry root | Sida cordifolia | 1 part |
| 27 | Patola frsh whole plant | Trichosanthes dioica | 1 part |
| 28 | Guduchi fresh stem | Tinospora cordifolia | 1 part |
| 29 | Shatavari fresh root | Asparagus racemosus | 1 part |
| 30 | Tulasi fresh leaves | Ocimum sanctum | 1 part |
| 31 | Kaidarya fresh leaves | Murraya koeinigii | 1 part |
| 16 | Jala Avashesha (Reduced to) | Water | 496 parts ⅛ part of water |

The bhasmas that are used in the various embodiments of the disclosed herbal composition may be prepared by methods that are generally known in the field. Bhasmas may be prepared by selecting genuine standard minerals as starting material such as Swarna makshika, steel iron, green vitriol etc; drying in a hot air oven; purifying the mineral by triturating, quenching, boiling, etc.; triturating the purified material with herbal decoction/juice; preparing into discs; drying of discs; preparing sharavasam puta, subjecting Sharavasam puta to Gaja puta, and powdering of discs once cooled. In an embodiment, the method is repeated 30 times till bhasma is obtained.

Figure 1B:
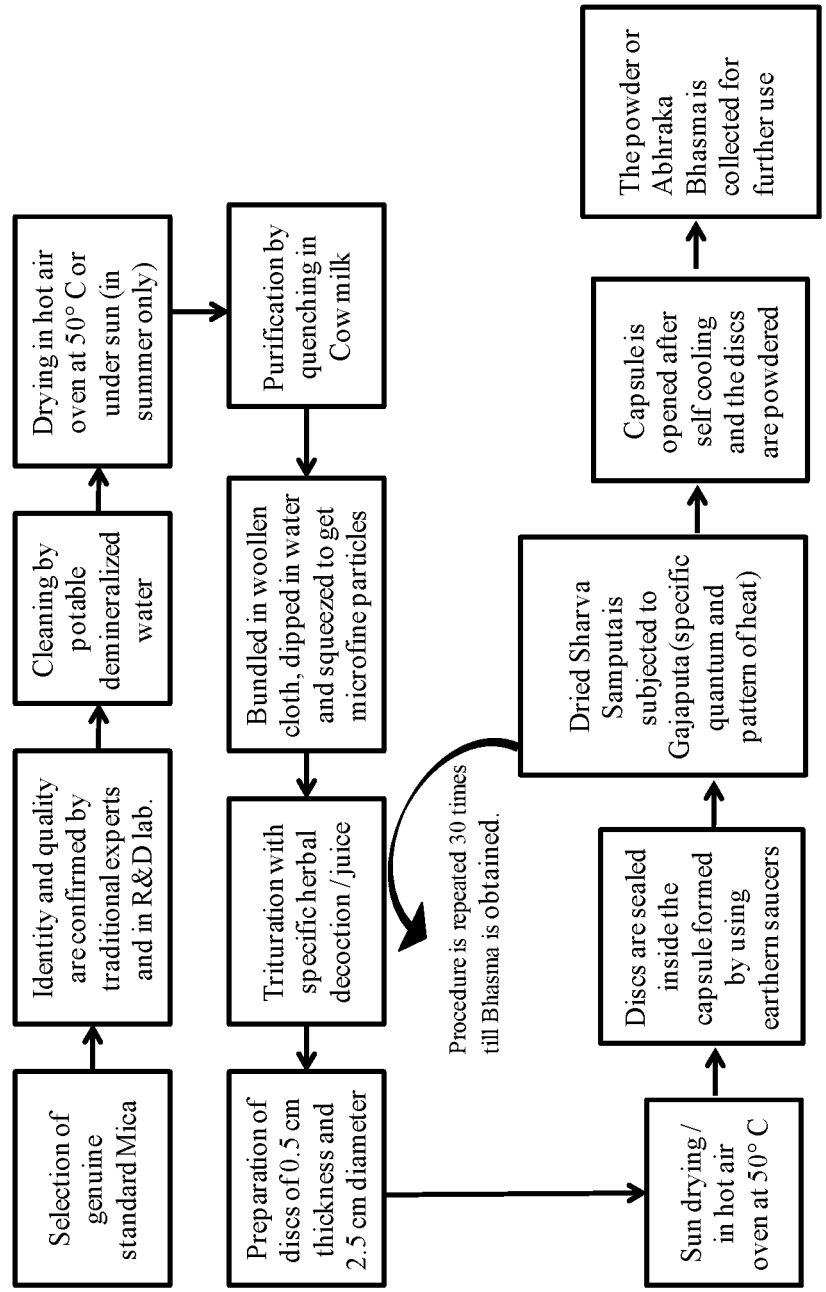
FIG. 1(b) depicts a flowchart for the preparation of Abhraka Bhasma, according to embodiments as disclosed herein.
Figure 1C:
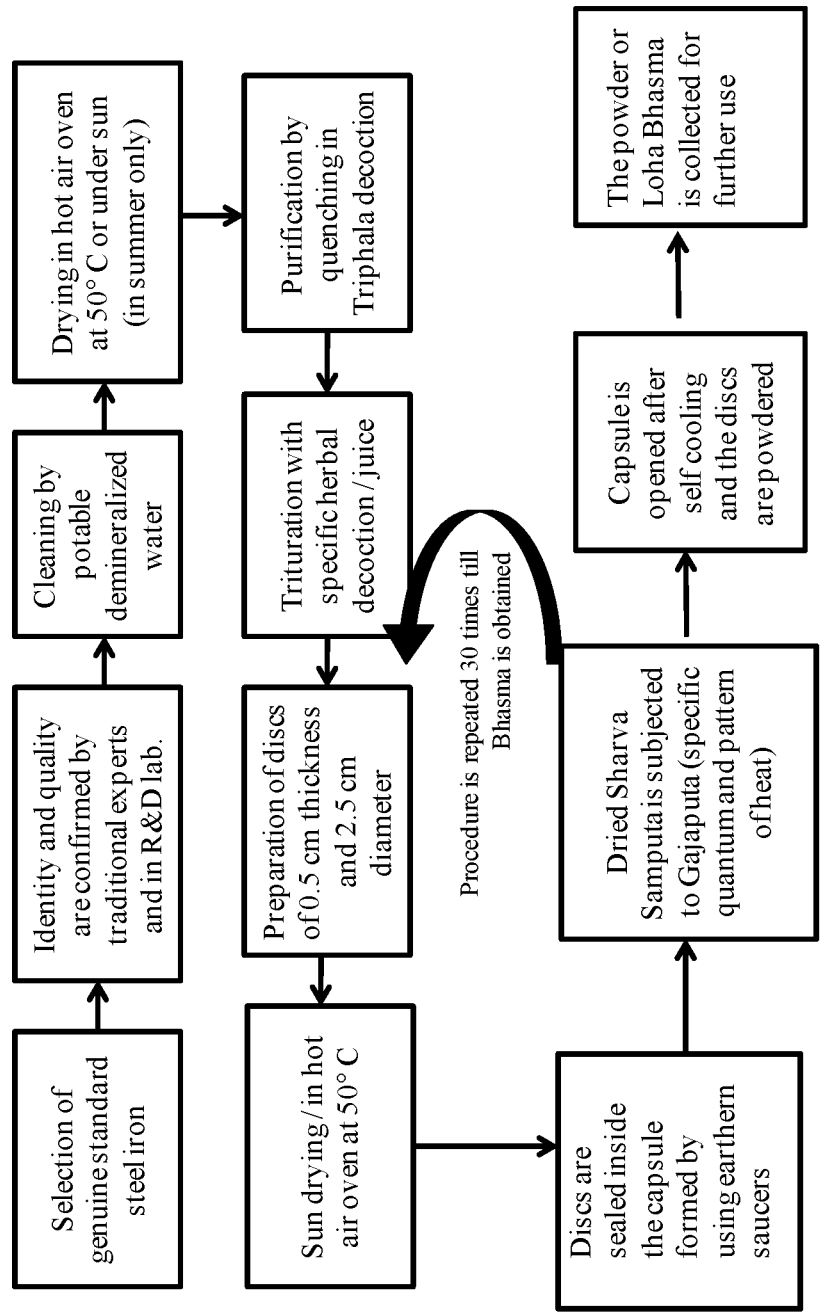
FIG. 1(c) depicts a flowchart for the preparation of Loha Bhasma, according to embodiments as disclosed herein.
Figure 1D:
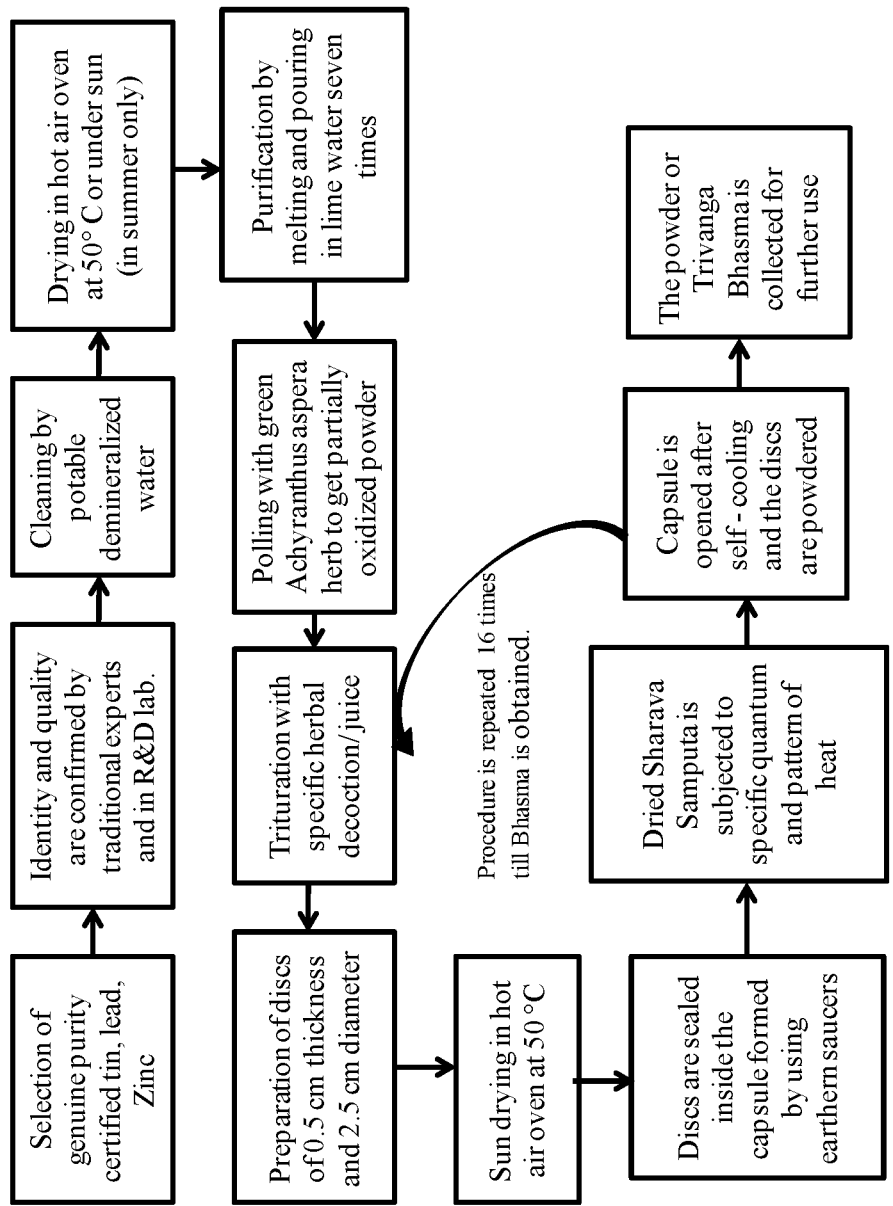
FIG. 1(d) depicts a flowchart for the preparation of Trivanga Bhasma, according to embodiments as disclosed herein.
Figure 1E:
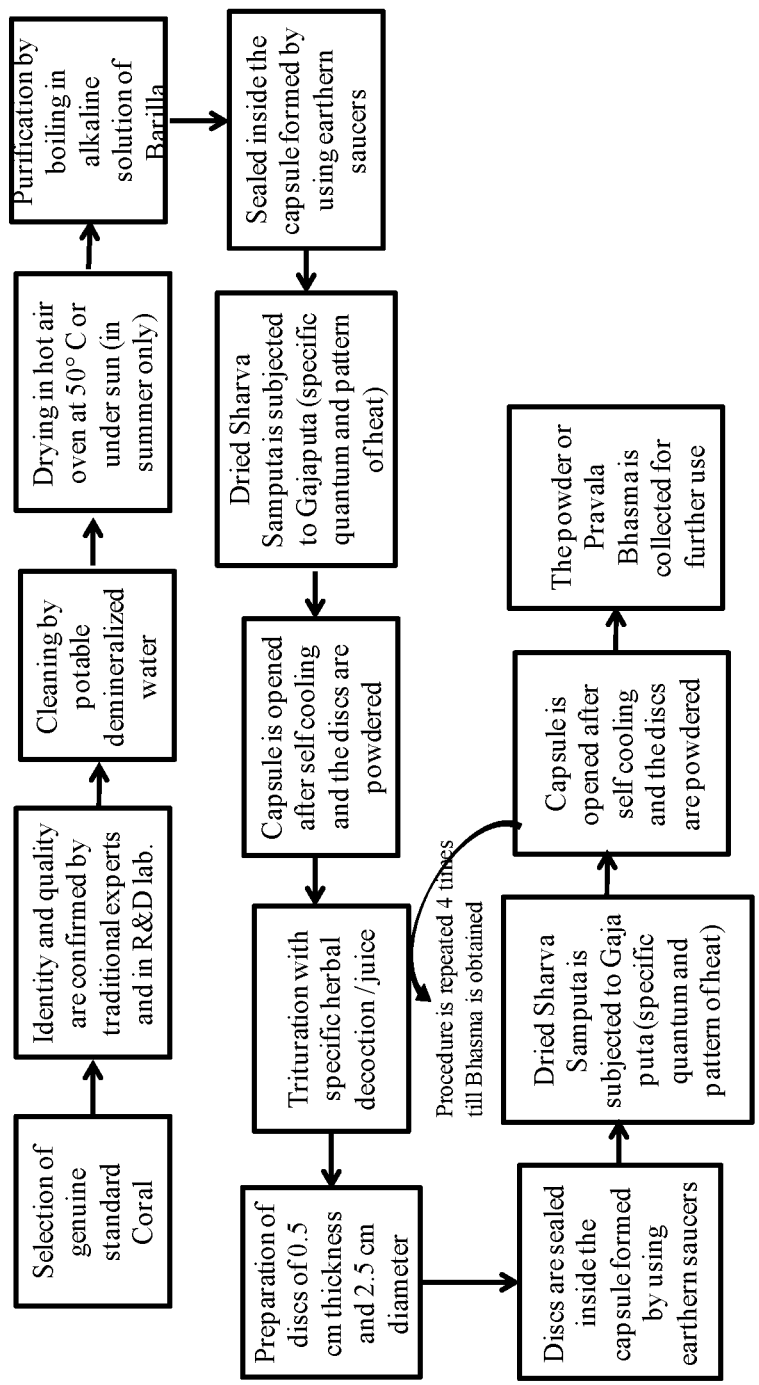
FIG. 1(e) depicts a flowchart for the preparation of Pravala Bhasma, according to embodiments as disclosed herein.

The starting materials used in the preparation of bhasmas may include standard minerals generally used in the field. In another embodiment, the preparation of Swarna makshika Bhasma includes Swarna makshika (Chalcopyrite) as the starting material. FIG. 1(a) depicts a flowchart for the preparation of Swarna makshika Bhasma using Swarna makshika as the starting material. In an embodiment, the preparation of Abhraka Bhasma includes mica as the starting material. FIG. 1(b) depicts a flowchart for the preparation of Abhraka Bhasma using mica as the starting material. In an embodiment, the preparation of Loha Bhasma includes steel iron as the starting material. FIG. 1(c) depicts a flowchart for the preparation of Loha Bhasma using steel iron as the starting material. In another embodiment, the preparation of Trivanga Bhasma includes alloy of tin, lead and zinc as the starting material. FIG. 1(d) depicts a flowchart for the preparation of Trivanga Bhasma using alloy of tin, lead and zinc as the starting material. In another embodiment, the preparation of Pravala Bhasma includes coral as the starting material. FIG. 1(e) depicts a flowchart for the preparation of Pravala Bhasma using coral as the starting material.

The purification, or shodhana, of the mineral may be performed by generally known methods in the field. In an embodiment, the purification may be by mixing the starting material with rock salt and lemon juice such as that in the preparation of Swarna makshika Bhasma. In another embodiment, the purification may be by quenching the mineral in Triphala decoction such as that in the preparation of Loha Bhasma. In another embodiment, the purification may be by quenching in Cow's milk such as that in the preparation of Abhraka Bhasma. In yet another embodiment, the purification may be by melting and pouring in lime water, preferably seven times, such as that in the preparation of Trivanga Bhasma. Further, in an embodiment, the purification may be by boiling in alkaline solution of Barilla such as that in the preparation of Pravala Bhasma.

The herbal decoction/juice used may be any herbal decoction/juice that is generally used for triturating in the preparation of bhasmas. For example, the herbal decoction/juice may include triphala, lemon juice, Gomutra (cow's urine) etc. In an embodiment, the herbal decoction used in the preparation of Swarna Makshika bhasma specifically includes Nimbu Swarasa (Lemon juice) and Kulatha Kwatha (Decoction of *Dolichos biflorus*). In another embodiment, the herbal decoction used in the preparation of Abhraka Bhasma specifically includes *Emblica officinalis, Terminalia chebula, Terminalia bellerica, Cyperus rotundus, Ficus bengalensis* and *Curcuma longa*. Table 4A depicts the list of herbs required for the herbal decoction used in trituration while preparing Abhraka Bhasma.

TABLE 4A

Herbal decoction used for trituration while preparing Abhraka Bhasma includes the following: Decoction of following:

| | | | |
|---|---|---|---|
| 1. | Amalaki dried fruit | Emblica officinalis | 1 part |
| 2. | Hareetaki dried fruit | Terminalia chebula | 1 part |
| 3. | Vibheetaki dried fruit | Terminalia bellerica | 1 part |
| 4. | Musta dried rhizome | Cyperus rotundus | 1 part |
| 5. | Vata dried root bark | Ficus bengalensis | 1 part |
| 6. | Haridra dried rhizome | Curcuma longa | 1 part |
| 7. | Jala Avashesha (Reduced to) | Water | 96 parts ⅛ part of liquid |

In another embodiment, the herbal juice useful in the preparation of Abhraka Bhasma specifically includes *Cassia occidentalis, Piper betle, Adhatoda vasica, Emblica officinalis, Alternathera sessilis, Amaranthus spinosus, Ricinus communis* and *Calotropis precera*, wherein it is. Table 4B depicts the list of herbs required for the herbal juice used in trituration while preparing Abhraka Bhasma.

TABLE 4B

Herbal juice used in trituration while preparing Abhraka Bhasma includes the following: Juice of following:

| | | | |
|---|---|---|---|
| 1. | Kasamarda fresh leaves | Cassia occidentalis | 1 part |
| 2. | Tambula fresh leaves | Piper betle | 1 part |
| 3. | Vasa fresh leaves | Adhatoda vasica | 1 part |
| 4. | Amalaki fresh fruit | Emblica officinalis | 1 part |
| 5. | Matsyakshi fresh plant | Alternathera sessilis | 1 part |
| 6. | Tanduleeyaka fresh plant | Amaranthus spinosus | 1 part |

TABLE 4B-continued

Herbal juice used in trituration while
preparing Abhraka Bhasma includes the following:
Juice of following:

| 7. | Eranda fresh leaves | *Ricinus communis* | 1 part |
| 8. | Arka fresh leaves | *Calotropis precera* | 1 part |

In an embodiment, the herbal decoction useful in the preparation of Loha Bhasma specifically includes *Emblica officinalis, Terminalia chebula, Terminalia bellerica, Crataeva nurvala, Boerhavia diffua, Bauhinia variegate* and Cow urine. Table 4C depicts the list of herbs required for the herbal decoction used in trituration while preparing Loha Bhasma. In another embodiment, the herbal decoction includes Triphala Kashaya (decoction of fruits of *Terminalia chebula, Terminalia bellerica* and *Emblica officinalis*), wherein it is useful in the preparation of Loha Bhasma.

TABLE 4C

Herbal decoction used in trituration while
preparing Loha Bhasma includes the following:
Decoction of following:

| 1. | Amalaki | *Emblica officinalis* | 1 part |
| 2. | Hareetaki | *Terminalia chebula* | 1 part |
| 3. | Vibheetaki | *Terminalia bellerica* | 1 part |
| 4. | Varuna | *Crataeva nurvala* | 1 part |
| 5. | Punarnava | *Boerhavia diffua* | 1 part |
| 6. | Kanchanara | *Bauhinia variegate* | 1 part |
| 7. | Gomutra | Cow urine | 48 parts |
| 8. | Jala | Water | 48 parts |
| | Avashesha (Reduced to) | | ⅛ part of liquid |

In an embodiment, the herbal decoction used in the preparation of Trivanga Bhasma specifically includes *Emblica officinalis, Terminalia chebula, Terminalia bellerica* and *Curcuma Longa*. Table 4D depicts the list of herbs required for the herbal decoction used in trituration while preparing Trivanga Bhasma.

TABLE 4D

Herbal decoction used in trituration while
preparing Trivanga Bhasma includes the following:
Decoction of following:

| 1. | Amalaki | *Emblica officinalis* | 1 part |
| 2. | Hareetaki | *Terminalia chebula* | 1 part |
| 3. | Vibheetaki | *Terminalia bellerica* | 1 part |
| 4. | Haridra dried rhizome | *Curcuma longa* | 1 part |
| 5. | Jala | Water | 64 parts |
| | Avashesha (Reduced to) | | ⅛ part of liquid |

In an embodiment, the herbal juice used in the preparation of Trivanga Bhasma specifically includes *Aloe vera* and *Aegle marmelos*. Table 4E depicts the list of herbs required for the herbal juice used in trituration while preparing Trivanga Bhasma.

TABLE 4E

Herbal juice used in trituration while
preparing Trivanga Bhasma includes the following:
Juice of following:

| 1. | Kumari fresh leaves | *Aloe vera* | 1 part |
| 2. | Bilva fresh leaves | *Aegle marmelos* | 1 part |

In an embodiment, the herbal juice used in the preparation of Pravala Bhasma specifically includes *Aloe vera, Aspara-gus racemosus, Sesbania sesban* and Cow milk. Table 4F depicts the list of herbs required for the herbal juice used in trituration while preparing Pravala Bhasma.

TABLE 4F

Herbal juice used in trituration while
preparing Pravala Bhasma includes the following:
Juice of following:

| 1. | Kumari fresh leaves | *Aloe vera* | 1 part |
| 2. | Shatavari fresh root | *Asparagus racemosus* | 1 part |
| 3. | Jayanti fresh leaves | *Sesbania sesban* | 1 part |
| 4. | Godugdha | Cow milk | 1 part |

Embodiments are further described herein by reference to the following examples. The following examples are included herein by way of illustration only and should not be construed to limit the scope of the claims provided herewith.

Example 1: Preparation of Swarna Makshika Bhasma

Firstly, the basic raw material is selected. The raw material used is Swarna Makshika i.e. Copper pyrite. Copper pyrite which looks yellow with iridescent tarnish having greenish black streak, uneven fracture, metallic luster, brittle tenacity, opaque with hardness between 3 and 4, specific gravity between 3.4 and 3.7 is selected. A sample of Swarna Makshika with, Copper: not <5%, Iron: not <20%, Sulphur: not <12% is selected. The selected raw material is washed with demineralized water to remove dirt and dried in hot air oven at about 50° C.

The raw material is then subjected to purification (Shodhana). For purification, at first the Swarna makshika is powdered in an iron mortar with an iron pestle. A clean and dry iron pan is then heated on a charcoal furnace onto which the powdered Swarna makshika and Saindhava Lavana (Rock salt) of about ⅓$^{rd}$ the amount of Swarna Makshika, is poured. This mixture is subjected to intense heat with frequent addition of lemon juice till the liberation of sulfur fumes stopped and it turns red. The process is completed in 3 days and the final product called Shodhita Swarna makshika obtained. This powder is added with water, mixed well, water is decanted to remove excess of salt. This powder is then dried under sun or in a hot air oven at about 50° C. to get a powder. The powder obtained is the purified Swarna Makshika.

The purified Swarna Makshika powder is triturated with lemon juice for about six hours till a soft homogenous paste or dough is obtained. The dough obtained is prepared into discs of 0.5 cm thickness and 2.5 cm diameter. The discs are dried under Sun or in a hot air oven at about 50° C. The dried discs are spread as a layer in an earthen saucer (Sharava). It is closed with another earthen saucer. The joint between the earthen saucers is sealed with mud plasters and dried to get a capsule (Sharava samputa). The dried earthen capsule containing the discs is subjected to heat using Gaja Puta (here, in a pit of 56.26×56.25×56.25 cubic cm, 250 cowdungs of standard size are filled) earthen capsule is placed on it. The vacant space is again filled with 125 cowdungs and lit with fire (here, specific quantum and pattern of heating is provided.). Further, the saucers are allowed to cool. After self-cooling (cooling by itself, without any external aid), the earthen saucer capsule is carefully collected, seal is removed, saucers separated and the material inside is collected. The collected partially incinerated Swarna Makshika discs are powdered and levigated with lemon juice. It is then again prepared into discs, dried, encapsulated and subjected to heat. This cycle from grinding with lemon juice till heating is repeated at least 10 times or till the Bhasma is properly prepared which is ascertained by specific generally known tests.

Example 2: Preparation of Abhraka Bhasma

The raw material, Abhraka (Biotite), and other ingredients procured from known authentic sources is thoroughly screened by Rasashastra experts based on the Grahya Lakshanas (ideal characteristics) mentioned in the classics.

The raw material is then subjected to purification (Shodhana of Abhraka). Specific quantity of Biotite mica is subjected to Shodhana by Nirvapa process (i.e. Heating & Quenching in liquid media) with the help of Triphala kwath (decoction of Triphala i.e. *Emblica officinalis, Terminalia chebula* and *Terminalia bellerica*) for 7 times. Each time fresh decoction is used for quenching, average temperature at the Red hot stage of Abhraka is around 739.00° C.

After the Shodhan process, purified mica is mixed with ¼ part of Dhanya (Unhusked rice-paddy) and taken in a jute bag, tied into a bolus. This bolus (Pottali) is then immersed in a big stainless steel vessel containing Kanji (sour gruel) and kept for 3 days (72 hours). On the 4th day the jute bag is opened and vigorously rubbed in same liquid media with both the hands till all Abhraka particles come out through pores of jute bag. It is allowed to settle down, kanji is decanted from vessel and Abhraka powder is collected which is referred as Dhanyabhraka.

The obtained Dhanyabhraka is now incinerated (Marana). For incineration, the Dhanyabhraka is levigated in Mortar & Pestle with specific decoction/juice (provided in Table 4A& Table 4B) in equal quantity by weight for at least 6 hrs till a homogeneous paste was formed, from which pellets (discs) are made of uniform size & shape (0.5×2.5 cm). Discs are dried under Sun or/in hot air oven at about 50° C. Dried discs are spread as a layer in an earthen saucer (Sharava). It is then closed with another earthen saucer. The joint between the earthen saucers is sealed with mud plasters and dried to get a capsule (Sharava samputa). Dried earthen capsule containing the discs is subjected to heat using Gaja Puta (here, in a pit of 56.26×56.25×56.25 cubic cm, 250 cow dungs of standard size are filled) earthen capsule is placed on it. Vacant space is again filled with 125 cowdungs and lit with fire (here, specific quantum and pattern of heating is provided).

Now, the saucers are allowed to cool. After self-cooling (cooling by itself, without any external aid), earthen saucer capsule is carefully collected, seal is removed, saucers separated and the material inside is collected. Content inside the earthen saucer capsule is powdered and levigated with herbal decoction/juice (provided in Table 4A& Table 4B). This cycle of levigation till incineration is repeated at least 30 times or till the Bhasma is properly prepared which is ascertained by specific generally known tests.

Example 3: Preparation of Loha Bhasma

The raw material, Iron turnings, and other ingredients procured from known authentic sources is thoroughly screened by Rasashastra experts and washed with demineralized water to remove dirt and dried in hot air oven at about 50° C.

The raw material is then subjected to purification by Samanya shodhana process and Vishesha shodhana process. In samanya shodhana process, specific quantity of raw material (Fe turning) is heated in Electric Muffle Furnace till red hot condition (~875-900° C.) and immersed in each medium viz. tila taila (sesame oil), takra (buttermilk), Gomutra (cow's urine), kanji (sour rice gruel), and kulattha kwatha (decoction of horse gram) and kept for self-cooling (approximately 1 h) at room temperature). This quenching process is repeated for seven times consecutively in tila taila followed by seven times consecutively in takra, gomutra, kanji, and kulattha kwatha by using fresh media every time. After completion of the process, material is filtered by Fe mesh and dried under sunlight. The material obtained at this stage is called samanya shodhita loha.

In vishesha shodhana process, quenching is done in *Triphala kwatha*. It is prepared by taking coarse powders of three myrobalans, taken without seed: *Haritaki (Terminalia chebula* Retz.), *Bibhitaki (Terminalia bellirica* [Gaertn.] Roxb.), and *Amalaki (Phyllanthus emblica* L.) in equal quantity and boiled in 8 parts of water till reduction to ¼th of the original volume of water to obtain *Triphala kwatha*. Using this, repeated quenching process of samanya shodhita loha is done. This purification step is repeated seven times using freshly prepared *Triphala kwatha*. The loha churna (coarse powder of Fe turning) obtained at this stage is called vishesha shodhita loha. The *Triphala kwatha* was prepared by heating equal quantity of Triphala to vishesha shodhita loha churna with two parts of water and reduced to ¼th of original volume. This *Triphala kwatha* was added to loha obtained after vishesha shodhana and allowed to dry under sunlight.

Further, Sthalipaka (Heating in vessel using fire) was performed. In this step, *Triphala kwatha* is prepared by taking Triphala, 3 parts of loha obtained after bhanupaka, and 16 parts of water was added to it. The whole material was boiled in a stainless steel container to reduce the volume to ⅛th of the original volume of water. Loha obtained after bhanupaka was washed with hot water and placed in a sthali (Fe pan), to which above freshly prepared *Triphala kwatha* was added and intense heating was given for complete evaporation of water contents of *Triphala kwatha*. On complete drying of the material, again *Triphala kwatha* was added and subjected to heat till dryness. It was further incinerated (Putapaka).

For incineration, freshly prepared Decoction as mentioned in Table 4C is mixed with the powder obtained after Sthali Paka in mechanized khalva yantra (mortar and pestle) and trituration is done with a frequency of 60 times/min. The paste formed during this trituration is made into cakrikas (pellets) and dried under sunlight. After complete drying of cakrikas, it is taken in an earthen vessel (sarava) and covered with another inverted earthen vessel. The space between the two earthen vessels was covered with clay smeared cloth; this specific process is known as *Sarava samputikarana* (sealed earthen saucers).

The dried earthen capsule containing the discs is subjected to heat using Gaja Puta (here, in a pit of 56.26×56.25× 56.25 cubic cm, 250 cowdungs of standard size are filled; earthen capsule is placed on it. Vacant space is again filled with 125 cowdungs and lit with fire (here, specific quantum and pattern of heating is provided.). After self-cooling (cooling by itself, without any external aid), earthen saucer capsule is carefully collected, seal is removed, saucers separated and the material inside is collected. This cycle from grinding with decoction till heating is repeated at least 30 times or till the Bhasma is properly prepared which is ascertained by specific tests.

Example 4: Preparation of Trivanga Bhasma

Purity certified, tin, lead and zinc are taken as basic raw materials. Samanya shodhana of Vanga, Naga & Yashada (General purification/detoxification procedure of tin, lead and zinc is performed). Dhalana method (melting and pouring into liquid) is adopted, where in raw Vanga (tin) is heated in an Iron ladle till it melts completely and then immediately poured into Kanji (sour rice gruel), Takra (butter milk), Kulatta kwatha (decoction of horse gram), Gomutra (cow urine) and Tila taila (sesame oil) through Pithara yantra (specific instrument). The process is repeated for 3 times each in five different liquid media, in the successive order and for every Dhalana fresh liquid media is taken. The same procedure is followed for the Samanya shodhana of Naga (lead) and Yashada (zinc) also.

Further, Vishesha shodhana of Vanga, Naga & Yashada (special purification of tin, lead and zinc) is performed. Dhalana method is adopted with the liquid media being Churnodaka (lime water) and the procedure is repeated for 7 times each with using fresh Churnodaka each time.

Jarana (partialoxidation by poling) of Trivanga was performed wherein, the shodhita (purified) Vanga, Naga & Yashada are melted in an iron pan by adding one after the other i.e., Yashada, Naga & Vanga in successive order. On molten Trivanga, little by little quantity of coarse powder of *Apamarga panchanga* (Whole plant of *Achyranthes aspera*) is added and stirring is done continuously with iron ladle. This process is continued till the Trivanga is converted into powder form, then it was covered with a Sharava and heated till the powder becomes red. After self-cooling, Jarita Trivanga is added with water, macerated and allowed to settle down over night. The next day morning supernatant water is decanted. The procedure is repeated for 3 days till it attained the pH 7, it is necessitated to remove excess Kshara (alkali).

Incineration (Marana) of Jarita Trivanga is then performed. Jarita Trivanga is subjected to levigation with decoction mentioned in table 4D and juices mentioned in table 4E and when the mixture attain proper consistency, chakrikas (pellets/discs of 0.5×2.5 cm dimension) are made and dried in hot air oven at 50° C. They are then placed in Sharavasamputa and subjected to Laghuputa (specific quantum of heat). The procedure was repeated for 16 times till all the characteristic features of Bhasma are obtained.

Example 5: Preparation of Pravala Bhasma

Selection of genuine raw material and authentication is performed by collection of good quality coral from a known source followed by authentication with the help of mineralogical tools.

Further, shodhana or Classical method of purification is performed. For purification, pieces of coral are washed in demineralized water, dried in hot air oven at 50° C., wrapped by a clean, starch less cloth and tied into a bolus. This bolus is suspended with the help of a thread from an iron rod placed at the inlet of an earthen pot. Inside the pot Saja Kshara (Barilla) dissolved in water is taken. Height of the bolus is maintained in such a way that it does not touch the base of the pot but remains immersed in the liquid throughout the procedure. Pot is heated at a temperature between 65 to 80° C. for three hours. Then the cloth bolus is opened, purified coral is removed, washed with hot water and dried.

For incineration (Marana), purified coral pieces are sealed in earthen saucer capsule and subjected to Gaja Puta (here, in a pit of 56.26×56.25×56.25 cubic cm, 250 cowdungs of standard size are filled) earthen capsule is placed on it. Vacant space is again filled with 125 cowdungs and lit with fire. (Here, specific quantum and pattern of heating is provided.)

After self-cooling (cooling by itself, without any external aid), earthen saucer capsule is carefully collected, seal is removed, saucers separated and the material inside is collected. The content inside the earthen saucer capsule is powdered and levigated with specified juice for about six hours till a soft homogenous paste is obtained. The dough obtained is prepared into discs of 0.5 cm thickness and 2.5 cm diameter. Discs are dried under Sun or/in hot air oven at 50° C. The dried discs are spread as a layer in an earthen saucer (Sharava). It is closed with another earthen saucer. The joint between the earthen saucers is sealed with mud plasters and dried to get a capsule (Sharava samputa). Dried earthen capsule containing the discs is subjected to heat using Gaja Puta. This cycle is repeated four times using different juice mentioned in Table 4F each time for levigation. After 4 such cycles of incineration Pravala Bhasma is formed.

Treatment

Disclosed herein are embodiments of a method of treatment and management of Thyroid dysfunction and associated complications. In the various embodiments herein, complications associated with thyroid dysfunction shall include any condition generally known to be associated with thyroid function such as Hashimoto's thyroiditis, hyperthyroidism, hypothyroidism. Goiter. Thyrotoxicosis, Graves' disease, autoimmune thyroiditis, etc. The embodiments disclosed herein also include a method of improving thyroid function in hyperthyroidic and hypothyroidic conditions. Further embodiments disclosed herein also include a method for treatment and management of thyroid disorders and symptoms associated with thyroid disorders such as Weight gain, Depression, Skin dryness. Hair fall, Fatigue, Acid eructation, Constipation, Weight loss, Anxiety, Sweating, Tremors, Palpitation, Hair fall, Sleep disturbance, Diarrhoea, etc. Furthermore, embodiments disclosed herein also include methods for improving complications associated with thyroid dysfunction such as Lipid peroxidation (LPO) level, Superoxide Dismutase (SOD) activity, lipid profile (HDL, LDL and Triglycerides levels), C reactive protein (CRP) level, blood glucose, Catalase activity, Glutathione level, T3, T4, TSH levels, etc.

In an embodiment, the method includes administering a patient with the composition as described in any of the embodiments disclosed herein. The patient according to the various embodiments herein may include any individual in need of such treatment including but not limited to individuals having Thyroid dysfunction, and disorders or any complications generally known to be associated with thyroid dysfunction such as Hashimoto's thyroiditis, hyperthyroidism, hypothyroidism, Goiter, Thyrotoxicosis, Graves' disease, autoimmune thyroiditis, etc. The patient may further include any individual looking to improving thyroid function. Further, the patient may also be any individual having complications associated with other organs such as hypothalamus and pituitary glands, thereby resulting in thyroid hormone imbalance. Furthermore, the patient may also include individuals having symptoms associated with thyroid disorders. Individuals prone to pre-natal or post-natal thyroid dysfunction may also be considered as suitable candidates for treatment by the disclosed embodiments.

In another embodiment, the method includes administering to a patient a composition having *Bauhinia variegata* (10 to 14 wt %), *Crataeva nurvala* (10 to 14 wt %) and *Commiphora mukul* (8 to 12 wt %); at least one of *Emblica officinalis* (2 to 6 wt %), *Terminalia chebula* (≤3 wt %), *Terminalia bellerica* (≤3 wt %), *Zingiber officinale* (≤3 wt %), *Piper nigrum* (≤3 wt %), *Piper longum* (≤3 wt %),

*Cinnamomum zeylanica* (≤3 wt %), *Elettaria cardamomum* (≤3 wt %), *Cinnamomum tamala* (≤3 wt %), *Glycerrhiza glabra* (≤3 wt %), *Boerhavia diffusa* (≤3 wt %), *Adhtatoda vasica* (≤3 wt %), *Vinca rosea* (≤3 wt %), *Withania somnifera* (≤3 wt %), *Sida cordifolia* (≤3 wt %), *Tinospora cordifolia* (≤3 wt %), *Ocimum sanctum* (≤3 wt %), *Curcuma longa* in an amount of ≤3 wt %, *Moringa oleifera* (≤3 wt %), *Aristolochia indica* (≤3 wt %), *Azadirachta indica* (≤3 wt %) and *Eclipta alba* (≤2 wt %); at least one of Swarna Makshika bhasma (≤2 wt %), Abhraka bhasma (≤2 wt %), Loha bhasma (≤2 wt %), Trivanga bhasma (≤2 wt %), Pravala bhasma (≤2 wt %) and *shilajit* (2 to 6 wt %); and a suitable excipient.

In an embodiment, the patient may be any individual in need of such treatment including ones having/suspected of having Thyroid dysfunction and associated complications. The patient may be any individual having/suspected of having complications associated with Thyroid such as Hypothroidism, Autoimmune thyroiditis Eg. Hashimoto's Thyroiditis, etc. Further, the patient may also be any individual having/suspected of having complications associated with other organs such as hypothalamus and pituitary glands, thereby resulting in thyroid hormone imbalance. In an embodiment, the disclosed composition may also be used to prevent Thyroid dysfunction and associated complications.

The patient may be administered a therapeutically effective amount of the embodiments of the disclosed composition. The therapeutically effective amount may vary depending on the patient. In an embodiment, the therapeutically effective amount is 500 to 1000 mg administered one to three times a day. Embodiments of the disclosed composition (also referred as Test drug or product) were tested for safety and efficacy, as described hereunder by way of examples. Embodiments are described herein by reference to the following examples by way of illustration only and should not be construed to limit the scope of the claims provided herewith.

Example 6: Safety Study

The Test drug was evaluated for toxicity as per OECD guidelines. Test drug was administered once orally to overnight fasted female Wistar rats at 2000 and 5000 mg/kg body weight (2 steps/dose; 3 animals/step) at a dose volume 10 ml/kg. Body weight was recorded on day 0, 7 and 14. Mortality/Clinical signs were observed at approximately 30 minutes, 1, 2 and 4 h on day 0 (after test drug administration) and thereafter once daily for 14 days.

All the experimental animals showed gain in body weight on day 7 and 14 in comparison to their day 0 body weight. No clinical signs and mortality were observed for 14 days in all experimental animals. No gross lesions were detected in animal treated with 2000 mg/kg body weight, whereas in animal number 8, treated with 5000 mg/kg body weight shows multifocal point of congestion in lungs. No gross lesions were detected in all other organs of experimental animals treated with 5000 mg/kg body weight.

Histopathologic examination of lungs of animal number 8 revealed alveolar haemorrhages, alveolar thickening with mononuclear cells infiltration and multifocal aggregates of mixed population of inflammatory cells around blood vessels and bronchioles.

Based on the above observations, the LD50 value of "Test drug" was found to be greater than 5000 mg/kg body weight and classified as Category-5 or unclassified based on Globally Harmonised Classification System (GHS) for Chemical Substances and Mixtures.

Example 7: Efficacy Study

Abstract:

The Test drug was evaluated clinically among 12 patients of Autoimmune thyroiditis. Seven patients were presented with the features of hypothyroidism and remaining five patients were of hypothyroidism. Patients were evaluated for the improvement in clinical features, thyroid function tests (comprising of T3, T4 and TSH) and also oxidative stress parameters including lipid peroxidation (LPO), reduced glutathione content (GSH), superoxide dismutase (SOD) and catalase activity (CAT). In addition to the improvement in clinical parameters and thyroid function test results, present findings revealed decrease in LPO level and increase in level of GSH, SOD and CAT activity by the treatment of Test drug, indicating reduction in oxidative stress in hypothyroid and hyperthyroid state. Hence, the Test drug is useful in management of both hypothyroidism and hyperthyroidism, and its primary mode of action looks to be anti-oxidant effect.

Experimental Details:

Materials and Methods: Patients with thyroid disorders (both hypo and hyperthyroidism) of either sex were randomly selected for the study. This work was carried out in accordance with ethical guidelines prescribed by Central Ethics Committee on Human Research after obtaining the concurrence of institutional ethical committee. Detailed history was recorded in the specially designed proforma and clinical presentations were recorded. As T3 and T4 were normal in most of the cases, TSH was considered as a parameter of assessment. All the chemicals which were used for this study were of analytical grade. Evaluation of oxidative stress parameters were done by various conventional methods such as lipid peroxidation (LPO), reduced glutathione content (GSH), superoxide dismutase (SOD) and catalase activity (CAT).

Dosage and Duration:

Tablet Test drug was administered at a dose of 2 tablets twice daily after food by swallowing with water as Anupana. Evaluation was done after three months medication.

Lipid Peroxidation Assay:

For determination of lipid peroxidation (LPO), the blood was withdrawn from retro-orbital plexus and was taken in the centrifuge tube containing anticoagulant. From this 5% suspension of RBC in 0.1 M phosphate buffered saline was prepared. To 2 ml of this 5% suspension, 2 ml of 28% trichloroacetic acid was added and centrifuged. After centrifugation the supernatant was separated. To 4 ml of supernatant 1 ml of 1% thiobarbituric acid was added, heated in boiling water for 60 minutes and cooled immediately. The absorbance was measured spectrophotometrically at 532 nm. The lipid peroxidation was calculated on the basis of the molar extinction coefficient of malondialdehyde (MDA) ($1.56 \times 10^5$) and expressed in terms of nanomoles of MDA/g Hb.

Reduced Glutathione Assay:

Glutathione activity was measured in whole blood. The blood (0.2 ml) was added to 1.8 ml of distilled water followed by 3.0 ml of precipitating mixture (1.67 gms of metaphorsphoric acid, 0.2 gms of EDTA, 30 gms NaCl to make 100 ml of solution). It was centrifuged at 2000 rpm for 5 minutes. Supernatant (1 ml) was added to 1.5 ml of phosphate solution followed by addition of 0.5 ml of DTNB reagent. The optical density was measured at 412 nm using spectrophotometer.

Superoxide Dismutase Assay:

The activity of SOD was determined in the erythrocyte lysate prepared from the 5% RBC suspension. To 50 ml of the lysate, 2 ml of 75 mM of Tris-HCl buffer (pH 8.2), 0.6 ml of 30 mM of EDTA and 0.3 ml of 2 mM of pyrogallol were added. An increase in the absorbance was measured at 420 nm for 3 minutes using spectrophotometer. One unit of enzyme activity is 50% inhibition of the rate of auto-oxidation of pyrogallol, as determined by change in absorbance/minute at 420 nm.

Catalase Assay:

The activity of catalase enzyme was determined in erythrocyte lysate. The lysate (50 ml) was taken and added to a test tube containing 2 ml of phosphate buffer (pH 7.0) and then 1 ml of 30 mM of H2O2 was added to it. The decrease in absorbance was measured at 240 nm for 1 minute using spectrophotometer.

Results:

Statistical analysis: Values were expressed as mean±SEM (n=6). All data were analysed by One-Way ANOVA. The level of significance was considered at $p<0.05$ and $p<0.01$. The results of study were divided into three parameters:

Clinical parameters
Thyroid function tests
Oxidative stress parameters

Clinical Parameters:

These parameters were studied before and after the dosage regimen of Test drug and the results are shown hereunder. Hypothyroid and hyperthyroid patients exhibited the symptoms like anxiety, depression, acidity, constipation etc. These patients showed significant reversal in the symptoms after the treatment with Test drug. Tables 5 depicts the effects of Test drug on clinical features of Hypothyroidism.

TABLE 5

| Parameters | Before treatment | After treatment |
| --- | --- | --- |
| Weight gain | ++ | + |
| Depression | ++ | + |
| Skin dryness | ++ | − |
| Hair fall | +++ | + |
| Fatigue | ++ | − |
| Acid eructation | ++ | − |
| Constipation | ++ | + |

Tables 6 depicts the effects of Test drug on clinical features of Hyperthyroidism.

TABLE 6

| Parameters | Before treatment | After treatment |
| --- | --- | --- |
| Weight loss | ++ | − |
| Anxiety | ++ | + |
| Sweating | ++ | − |
| Tremors | ++ | − |
| Palpitation | +++ | − |
| Hair fall | ++ | + |
| Fatigue | ++ | − |
| Sleep disturbance | ++ | − |
| Diarrhoea | ++ | − |

Thyroid Function Tests:

TSH level in hypothyroidism patients showed a marked reduction from 12.55 to 3.25 on an average. These patients however had normal T3 and T4 levels. Among the patients of hyperthyroidism average TSH level was significantly improved along with corresponding changes in T3 and T4 levels. Tables 7 depicts the results of Thyroid test function in Hypothyroidism.

TABLE 7

| Parameters | Before treatment | After treatment |
| --- | --- | --- |
| TSH | 12.55 | 3.25 |

Table 8 depicts the results of Thyroid test function in Hyperthyroidism.

TABLE 8

| Parameters | Before treatment | After treatment |
| --- | --- | --- |
| $T_3$ | 363 | 185 |
| $T_4$ | 16.5 | 10.7 |
| TSH | 1.55 | 4.55 |

Oxidative Stress Parameter:

Lipid Peroxidation Assay:

In normal control group the LPO levels (0.8339±0.1361) showed insignificant decrease in Test drug treated control group; whereas in hypothyroid and hyperthyroid group, the LPO levels (6.819±0.8946) and (10.17±0.9115) respectively showed significant decrease with the treatment of Test drug. The results are depicted in the table provided hereunder. Thus, the marked increase in the oxidative stress was found in hypothyroid and hyperthyroid groups as indicated by increase in LPO levels, whereas treatment with Test drug showed reduction in oxidative stress. Table 9 depicts the effect of Test drug on Lipid peroxidation level.

TABLE 9

| | Lipid peroxidation (nM of MDA/gHb) | |
| --- | --- | --- |
| Groups | Normal | Test drug treated |
| Control | 0.8339 ± 0.1361 | 0.8288 ± 0.1100 |
| Hypothyroid | 6.819 ± 0.8946* | 2.789 ± 0.4783** |
| Hyperthyroid | 10.17 ± 0.9115* | 3.371 ± 0.4723** |

Values are mean ± SEM, (n = 12).
*$p < 0.05$, when compared to respective normal group.
**$p < 0.01$, when compared to respective diseased group (hypothyroid and hyperthyroid).

Reduced Glutathione Assay:

In normal control group the GSH content (2.068±0.3168) showed insignificant increase in Test drug treated control group; whereas hypothyroid and hyperthyroid group, the GSH content (0.1467±0.0230) and (0.1097±0.0139) respectively showed significant increase with the treatment of Test drug. The results are depicted in the table provided hereunder. Thus, the marked increase in the oxidative stress was found in hypothyroid and hyperthyroid groups as indicated by decrease in GSH content, whereas treatment with Test drug showed decrease in oxidative stress as indicated by the increased GSH content. Table 10 depicts the effect of Test drug on Glutathione level.

TABLE 10

| Groups | Reduced glutathione (μm DTNB conjugated/gHb) | |
| --- | --- | --- |
| | Normal | Test drug treated |
| Control | 2.068 ± 0.3168 | 2.088 ± 0.2471 |
| Hypothyroid | 0.1467 ± 0.0230* | 0.7599 ± 0.1052** |
| Hyperthyroid | 0.1097 ± 0.0139* | 0.7588 ± 0.1199** |

Values are mean ± SEM, (n = 12).
*$p < 0.05$, when compared to respective normal group.
**$p < 0.01$, when compared to respective diseased group (hypothyroid and hyperthyroid).

Superoxide Dismutase Assay:

In normal control group the SOD activity (5.365±0.8098) showed insignificant increase in Test drug treated control group; whereas in hypothyroid and hyperthyroid group, the SOD activity (0.4798±0.1326) and (0.4781±0.1041) showed significant increase with the treatment of Vitalex. The results are depicted in the table provided hereunder. Thus, the marked increase in the oxidative stress was found in hypothyroid and hyperthyroid groups as indicated by decreased in SOD activity, whereas treatment with Test drug showed decrease in oxidative stress as indicated by the increased SOD activity as compared to hypothyroid and hyperthyroid groups. Table 11 depicts the effect of Test drug on Superoxide Dismutase activity.

TABLE 11

| Groups | Superoxide dismutase (units/mg protein) | |
| --- | --- | --- |
| | Normal | Test drug treated |
| Control | 5.365 ± 0.8098 | 5.390 ± 0.9198 |
| Hypothyroid | 0.4798 ± 0.1326* | 2.759 ± 0.3175** |
| Hyperthyroid | 0.4781 ± 0.1041* | 2.698 ± 0.3189** |

Values are mean ± SEM, (n = 12).
*$p < 0.05$, when compared to respective normal group.
**$p < 0.01$, when compared to respective diseased group (hypothyroid and hyperthyroid).

Catalase Assay:

In normal control group the CAT activity (2.928±0.7428) showed insignificant increase in Test drug treated control group; whereas in hypothyroid and hyperthyroid groups, the CAT activity (0.3709±0.1193) and (0.2296±0.0923) showed significant increase with the treatment of Test drug. The results are depicted in the table provided hereunder. Thus, the marked increase in the oxidative stress was found in hypothyroid and hyperthyroid groups as indicated by decrease in CAT activity, whereas treatment with Test drug showed decrease in oxidative stress as indicated by the increased CAT activity as compared to hypothyroid and hyperthyroid groups. Table 12 depicts the effect of Test drug on Catalase activity.

TABLE 12

| Groups | Catalase (units/mg protein) | |
| --- | --- | --- |
| | Normal | Test drug treated |
| Control | 2.928 ± 0.7428 | 2.989 ± 0.4529 |
| Hypothyroid | 0.3709 ± 0.1193* | 1.819 ± 0.2204** |
| Hyperthyroid | 0.2296 ± 0.0923* | 1.688 ± 0.2822** |

Values are mean ± SEM, (n = 12).
*$p < 0.05$, when compared to respective normal group.
**$p < 0.01$, when compared to respective diseased group (hypothyroid and hyperthyroid).

Table 13 depicts the effect of Test drug on lipid profile, CRP and blood glucose parameters.

TABLE 13

| Parameters | Baseline | Post treatment |
| --- | --- | --- |
| Total cholesterol | 236.4 ± 15.1 | 203.2 ± 14.7*** |
| LDL | 162.9 ± 12.8 | 144.3 ± 10.4*** |
| Triglyceride | 219.9 ± 26.9 | 168.1 ± 21.5*** |
| HDL | 39.9 ± 4.1 | 43.14 ± 3.2*** |
| C Reactive protein | 5.9 ± 0.9 | 5.1 ± 0.8*** |
| Blood glucose | 10.6.3 ± 15.3 | 91.8 ± 11.6*** |

Data are expressed as Mean ± SD,
***$p < 0.001$ as compared to baseline levels

Table 14 depicts the Safety evaluation of test drugs on hepatic and renal parameters

TABLE 14

| Biochemical parameters | Visit 1 (day 0) | Visit 2 (Day 21) | Visit 3 (Day 35) |
| --- | --- | --- | --- |
| ALT (IU/L) | 28.5 ± 4.6 | 25.8 ± 3.5 | 30.2 ± 3.4 |
| AST (IU/L) | 28.8 ± 4.1 | 27.6 ± 3.9 | 30.3 ± 4.3 |
| ALP (IU/L) | 142.6 ± 17.9 | 141.1 ± 17.7 | 144.6 ± 17.8 |
| Bilirubin (mg/dL) | 0.80 ± 0.18 | 0.84 ± 0.17 | 0.88 ± 0.16 |
| Urea (mg/dL) | 28.5 ± 5.3 | 28.9 ± 5.2 | 29.8 ± 5.2 |
| Creatinine (mg/dL) | 0.83 ± 10 | 0.83 ± 0.09 | 0.89 ± 0.14 |
| B2MG (mg/dL) | 1.08 ± 0.4 | — | 1.11 ± 0.3 |
| NGAL (mg/mL) | 36.4 ± 9.2 | — | 36.2 ± 7.1 |

CONCLUSION

Marked relief observed in clinical features of thyroid dysfunction is due to the total effect of ingredients used in the product. In total it can be concluded that Test drug tablet is a promising drug in both hypo and hyperthyroidism especially when the cause is auto immune thyroiditis.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modification within the spirit and scope of the embodiments as described herein.

I claim:

1. An oral composition for treatment and management of thyroid dysfunction and associated complications, comprising therapeutically effective amount of *Bauhinia variegata, Crataeva nurvala, Commiphora mukul, Emblica officinalis, Terminalia chebula, Terminalia bellerica, Zingiber officinale, Piper nigrum, Piper longum, Cinnamomum zeylanica, Elettaria cardamomum, Cinnamomum tamala, Glycyrrhiza glabra, Boerhavia diffusa, Adhatoda vasica, Vinca rosea, Withania somnifera, Sida cordifolia, Tinospora cordifolia, Ocimum sanctum, Curcuma longa, Moringa oleifera, Aristolochia indica, Azadirachta indica, Eclipta alba, Shilajit*, at least one Bhasma, and a suitable excipient.

2. The composition as claimed in claim 1, wherein said Bhasma is selected from a group consisting of Swarna Makshika bhasma, Abhraka bhasma, Loha bhasma, Trivanga bhasma and Pravala bhasma.

3. The composition as claimed in claim 1, wherein said *Bauhinia variegata* is present in an amount ranging from 10 to 14 wt % of the total weight of the composition.

4. The composition as claimed in claim 1, wherein said *Crataeva nurvala* is present in an amount ranging from 10 to 14 wt % of the total weight of the composition.

5. The composition as claimed in claim 1, wherein said *Commiphora mukul* is present in an amount ranging from 8 to 12 wt % of the total weight of the composition.

6. The composition as claimed in claim 1, wherein said *Shilajit* is present in an amount ranging from 2 to 6 wt % of the total weight of the composition.

7. The composition as claimed in claim 2, wherein said composition comprises Swarna Makshika bhasma in an amount of ≤2 wt %, Abhraka bhasma in an amount of ≤2 wt %, Loha bhasma in an amount of ≤2 wt %, Trivanga bhasma in an amount of ≤2 wt % and Pravala bhasma in an amount of ≤2 wt %, of the total weight of the composition.

8. The composition as claimed in claim 1, wherein said composition comprises *Emblica officinalis* in an amount ranging from 2 to 6 wt %, *Terminalia chebula* in an amount of ≤3 wt %, *Terminalia bellerica* in an amount of ≤3 wt %, *Zingiber officinale* in an amount of ≤3 wt %, *Piper nigrum* in an amount of ≤3 wt %, *Piper longum* in an amount of ≤3 wt %, *Cinnamomum zeylanica* in an amount of ≤3 wt %, *Elettaria cardamomum* in an amount of ≤3 wt %, *Cinnamomum tamala* in an amount of ≤3 wt %, *Glycyrrhiza glabra* in an amount of ≤3 wt %, *Boerhavia diffusa* in an amount of ≤3 wt %, *Adhatoda vasica* in an amount of ≤3 wt %, *Vinca rosea* in an amount of ≤3 wt %, *Withania somnifera* in an amount of ≤3 wt %, *Sida cordifolia* in an amount of ≤3 wt %, *Tinospora cordifolia* in an amount of ≤3 wt %, *Ocimum sanctum* in an amount of ≤3 wt %, *Curcuma longa* in an amount of ≤3 wt %, *Moringa oleifera* in an amount of ≤3 wt %, *Aristolochia indica* in an amount of ≤3 wt %, *Azadirachta indica* in an amount of ≤3 wt % and *Eclipta alba* in an amount of ≤2 wt %, of the total weight of the composition.

9. The composition as claimed in claim 1, wherein said suitable excipient is gum acacia present in an amount in the range of 8 to 12 wt % of the total weight of the composition.

10. The composition as claimed in claim 1, comprising *Bauhinia variegata* in an amount ranging from 10 to 14 wt %, *Crataeva nurvala* in an amount ranging from 10 to 14 wt %, *Commiphora mukul* in an amount ranging from 8 to 12 wt %, *Shilajit* in an amount ranging from 2 to 6 wt %, Swarna Makshika bhasma in an amount of ≤2 wt %, Abhraka bhasma in an amount of ≤2 wt %, Loha bhasma in an amount of ≤2 wt %, Trivanga bhasma in an amount of ≤2 wt % Pravala bhasma in an amount of ≤2 wt %, *Emblica officinalis* in an amount ranging from 2 to 6 wt %, *Terminalia chebula* in an amount of ≤3 wt %, *Terminalia bellerica* in an amount of ≤3 wt %, *Zingiber officinale* in an amount of ≤3 wt %, *Piper nigrum* in an amount of ≤3 wt %, *Piper longum* in an amount of ≤3 wt %, *Cinnamomum zeylanica* in an amount of <3 wt %, *Elettaria cardamomum* in an amount of ≤3 wt %, *Cinnamomum tamala* in an amount of ≤3 wt %, *Glycyrrhiza glabra* in an amount of ≤3 wt %, *Boerhavia diffusa* in an amount of ≤3 wt %, *Adhatoda vasica* in an amount of ≤3 wt %, *Vinca rosea* in an amount of ≤3 wt %, *Withania somnifera* in an amount of ≤3 wt %, *Sida cordifolia* in an amount of ≤3 wt %, *Tinospora cordifolia* in an amount of ≤3 wt %, *Ocimum sanctum* in an amount of ≤3 wt %, *Curcuma longa* in an amount of ≤3 wt %, *Moringa oleifera* in an amount of ≤3 wt %, *Aristolochia indica* in an amount of ≤3 wt %, *Azadirachta indica* in an amount of ≤3 wt %, and *Eclipta alba* in an amount of ≤2 wt %, of the total weight of the composition; and a suitable excipient.

11. The composition as claimed in claim 10, wherein said composition is in the form of a tablet.

12. The composition as claimed in claim 11, wherein said tablet is in the form of 500 mg tablet.

\* \* \* \* \*